United States Patent [19]

Kaspers et al.

[11] 4,296,116

[45] Oct. 20, 1981

[54] FUNGICIDAL AGENTS, PROCESSES FOR THEIR PREPARATION AND THEIR USE FOR COMBATING FUNGI

[75] Inventors: Helmut Kaspers, Leverkusen; Wilhelm Brandes, Leichlingen, both of Fed. Rep. of Germany

[73] Assignee: Bayer Aktiengesellschaft, Leverkusen, Fed. Rep. of Germany

[21] Appl. No.: 88,688

[22] Filed: Oct. 26, 1979

[30] Foreign Application Priority Data

Nov. 16, 1978 [DE] Fed. Rep. of Germany ....... 2849695
Jul. 31, 1979 [DE] Fed. Rep. of Germany ....... 2931034

[51] Int. Cl.³ .................... A01N 43/76; A01N 41/06; A01N 43/80; A01N 43/50
[52] U.S. Cl. ................. 424/272; 424/273 R; 424/274; 424/321
[58] Field of Search ............... 424/267, 274, 276, 321, 424/272, 273 R

[56] References Cited

U.S. PATENT DOCUMENTS 3,903,090  9/1975  Fujinami et al. .................... 546/208

FOREIGN PATENT DOCUMENTS 2207576  8/1973  Fed. Rep. of Germany .
1310083  3/1963  France .

OTHER PUBLICATIONS

Pesticide Index, 4th Ed.-1969-Frear, pp. 88 & 233.
Kuehle et al., Chem. Abst. 76, 24913(v), 58,977(j), (1972).
Hansen et al., Chem. Abst. 78, 144,254(u), (1973).

*Primary Examiner*—Douglas W. Robinson
*Attorney, Agent, or Firm*—Sprung, Felfe, Horn, Lynch & Kramer

[57] ABSTRACT

A synergistic fungicidal composition comprising (1) at least one carboxidide of the formula

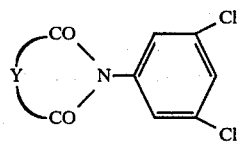

in which
Y represents a bifunctional group linking the two carbonyl groups with formation of an optionally substituted 5-membered heterocyclic ring with a total of 1 or 2 hetero-atoms (O and N), and (2)

$(CH_3)_2N-SO_2-N-S-CCl_2F$,

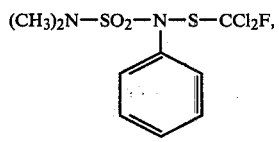

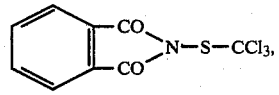

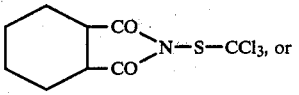

$(CH_3)_2N-SO_2-N-S-CCL_2F$

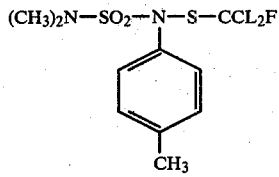

9 Claims, No Drawings

FUNGICIDAL AGENTS, PROCESSES FOR THEIR PREPARATION AND THEIR USE FOR COMBATING FUNGI

The present invention relates to new fungicidal synergistic combinations of certain known carboximides and the known compound N,N-dimethyl-N'-phenyl-N'-fluorodichloromethylthiosulphamide.

It is already known that some carboximides have a high fungicidal activity, in particular against the important harmful fungus *Botrytis cinerea* (in this context, see K. H. Büchel, "Pflanzenschutz and Schädlingsbekämpfung" ("Plant Protection and Pest Combating"), page 148, Georg Thieme Verlag, Stuttgart (1977)). However, when used in practice in the customary manner, for example in viniculture, plant damage occasionally occurs, which restricts the general applicability of these agents.

The present invention now provides a fungicidal composition containing as active ingredients (1) a carboximide of the general formula

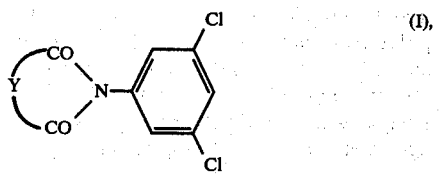

in which
Y represents a bifunctional group linking the two carbonyl groups with formation of an optionally substituted 5-membered heterocyclic ring with a total of 1 or 2 hetero-atoms (O and N),
and (2) N,N-dimethyl-N'-phenyl-N'-fluorodichloromethylthiosulphamide (short name: "Dichlofluanid"), of the formula

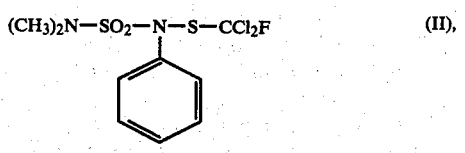

alone or in admixture with a solid or liquid or liquefied gaseous diluent or carrier.

Surprisingly, the active compound combination according to the invention not only has a high fungicidal activity, but, in particular, is also tolerated very well by plants. A valuable enrichment of the art is thereby achieved.

The general formula (I) provides a definition of the carboximides required for the active compound combination according to the invention. In this formula, Y preferably represents the following bifunctional groups

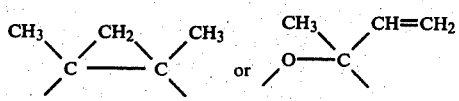

The compounds of the formulae

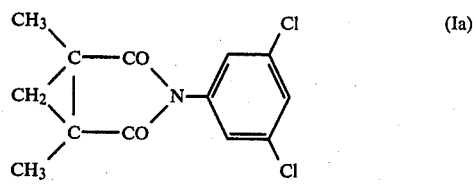

(short name: "Procymidor") and

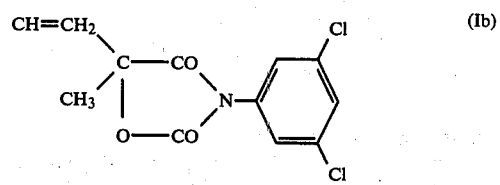

(short name: "Vinchlozolin") are thus particularly preferred.

The compounds of the formulae (Ia) and (Ib) are known (see the textbook by K. H. Büchel, mentioned above, and R. Wegler, "Chemie der Pflanzenschutz und Schädlings-bekämpfungsmittel" ("Chemistry of Plant Protection Agents and Agents for Combating Pests"), Volume 4, pages 202 and 217, Springer-Verlag, Berlin/Heidelberg/New York (1977)) and are also applied in agricultural practice. The preparation of the active compounds is likewise known (see, for example, the statements in the standard work by R. Wegler mentioned above, and U.S. Pat. No. 3,903,090 (for Ia) and DT-OS (German Published Specification) No. 2,207,576 (for Ib)).

Simultaneous application of the compound of the formula (Ia) and of the compound of the formula (II) is particularly preferred, an increase in the toleration by plants being achieved in relation to the results obtained with the carboximides of the formula (I) by themselves.

However, simultaneous application of the compounds of the formulae (I) and (II) not only reduces the toleration risk, but also simplifies the plant protection measures. In one operation, it is possible, for example, to combat the most important vine diseases caused by fungi, since Dichlofluanid (II) has the action against vine Peronospora (*Plasmopara viticola*) and against fire disease (*Pseudopeziza tracheiphila*), which in the case of some of the carboximides is only slight, and is officially permitted in the Federal Republic of Germany, for example, for these indications (1978 Plant Protection Agent Register of the Federal Biological Institute for Land and Forestry).

The compound of the formula (II) has already been generally known for a relatively long time, as have its preparation and fungicidal action (for details see R. Wegler (op. cit.), Volume 2, pages 94–95 and Volume 4, pages 193–194).

Instead of the active compound of the formula (II), it is also possible in some cases to use similar N-polyhalogenoalkylthio derivatives of amido compounds and imido compounds. Examples of such compounds which may be mentioned are N-trichloromethylthiophthalimide and the corresponding tetrahydro compound thereof, which are two compounds which have already been known as plant protection fungicides for a long time (for details see R. Wegler (op. cit.), Volume 2, pages 108-109 and Volume 4, pages 190-192), and have the formulae

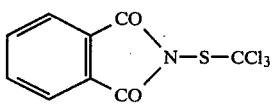
(III)

(short name: "Folpet") and

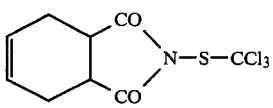
(IV)

(short name: "Captan").

Furthermore, the 4-methylphenyl derivative of the compound (II), with the short name "Tolylfluanid" may also be mentioned at this point (see R. Wegler (op. cit.), Volume 4, page 194).

The weight ratios of the two groups of active compounds in the active compound combinations according to the invention can vary within relatively wide ranges. In general, 0.5 to 8 parts by weight, preferably 1 to 4 parts by weight, of component (2), in particular N,N-dimethyl-N'-phenyl-N'-fluorodichloromethylthio-sulphamide, are present per part by weight of component (1), that is the carboxamide(s).

The active compound combinations according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compound combinations, at the concentration required for combating plant diseases, permits treatment of above-ground parts of plants, of vegetative propagation stock and seeds, and of the soil.

The active compounds can be converted into the customary formulations, such as solutions, emulsions, powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules or inorganic and organic meals, and granules or organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylenefatty alcohols ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compound combinations can be used as such or in the form of their formulations or the use forms prepared therefrom by further dilution, such as ready-to-use use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, from 1 to 0.0001% by weight, preferably from 0.5 to 0.001%.

In the treatment of seed, amounts of active compound of 0.001 to 50 g, preferably 0.01 to 10 g, are generally employed per kilogram of seed.

For the treatment of soil, active compound concentrations of 0.00001 to 0.1% by weight, preferably 0.0001 to 0.02%, are required at the place of action.

The invention also provides a method of combating fungi which comprises applying to the fungi, or to a habitat thereof, a composition according to the present invention.

The invention also provides crops protected from damage by fungi by being grown in an area in which immediately prior to and/or during the time of the growing a composition of the present invention was applied.

The following Examples 1 and 2 show how a striking improvement in the toleration by plants can be achieved when (1) carboximides of the formula (1) and (2) Dichlofluanid, of the formula (II) are applied simultaneously. As can be seen from the test results, the positive effect of the active compound component (2) (Dichlofluanid) can be demonstrated on all the varieties tested, independently of the test year. As is also shown in Example 3, the fungicidal action of the known individual compounds is not impaired by applying them simultaneously in the active compound combination accordng to the invention; rather, an improvement in the action can be concluded from the test results.

EXAMPLE 1

Test unit with artificial rain for the purpose of producing high atmospheric humidity and long wet-leaf times.

The vines were sprayed with the preparation of active compound until dripping wet 4 times. The spraying interval was in each case 4 to 10 days. In order to provoke damage, the plants were subjected to artificial rain between successive treatments. 6 days after the 4th treatment, the damage to the leaves of the vine plants was investigated.

The tests were carried out in 1977 on vines of the Müller-Thurgau variety.

The vines were treated with the known individual active compounds (Ia) (Procymidor), (Ib) (Vinchlozolin) and (II) (Dichlofluanid), and with combinations, according to the invention, of (Ia) and (II) in ratio of 2:3 and of (Ib) and (II) in a ratio of 2:3. A considerably higher tolerance by plants was found in the case of the combinations than in the case of the individual active compounds of the carboximide series.

EXAMPLE 2

The tests were carried out with different varieties in normal vineyards:

After blossoming, the vines were treated twice with the active-compound preparation (spray liquor). The amount applied per hectare was about 2,000 liters. Spraying took place in each case on moist leaves late in the evening. 2 weeks after the last treatment, the damage to the leaves of the vine plants was rated in percent.

The following varieties of vine were investigated: Bacchus, Faber, Kerner, Morio-Muskat, Müller-Thurgau, Riesling and Sissi.

The vines were treated with the known individual active compounds (Ia) (Procymidor) and (II) (Dichlofluanid), and with combinations, according to the invention, of (Ia) and (III) (Folpet) and (Ia) and (II), in each case in a ratio of 1:2. A high tolerance by plants was found in the case of the combinations.

EXAMPLE 3

Botrytis test (lettuce)/protective

Commercially available formulations were dispersed in tapwater in the required application amounts or concentrations and the resulting aqueous dispersions were used.

Lettuce plants in the 8–10 leaf stage were sprayed with the spray liquid until dripping wet. After 24 hours 2 small pieces of agar covered with *Botrytis cinerea* were placed on each leaf. The inoculated plants were placed in a darkened, moist chamber at 20° C. 3 days after the inoculation, the size of the infected spots on the leaves was rated.

The ratings obtained were converted to percent infection. 0% denoted no infection and 100% meant that the plants were completely infected.

The active compounds, active compound concentrations and results can be seen from the table which follows.

TABLE 1

*Botrytis* test (lettuce)/protective

| Active compound | Active compound concentration (%) | Infection in (%) |
| --- | --- | --- |
| Individual active compounds: | | |
| Ia (Procymidor) | 0.01 | 16 |
| II (Dichlofluanid) | 0.04 | 30 |
|  | 0.01 | 100 |
| Combinations according to the invention: | | |
| Ia ⎫ (1:1) | 0.01 | 12 |
| II ⎭ | 0.01 | |
| Ia ⎫ (1:4) | 0.01 | 8 |
| +11 ⎭ | 0.04 | |

It will be appreciated that the instant specification and examples are set forth by way of illustration and not limitation, and that various modifications and changes may be made without departing from the spirit and scope of the present invention.

What we claim is:

1. A fungicidal composition comprising a fungicidally effective amount of (1) at least one carboximide of the formula

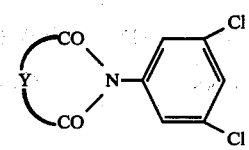

in which

Y represents a bifunctional group linking the two carbonyl groups with formation of an optionally substituted 5-membered heterocyclic ring with a total of 1 or 2 hetero-atoms (O and N), and (2),

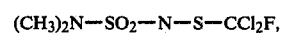

-continued

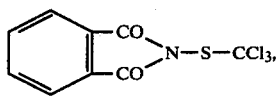

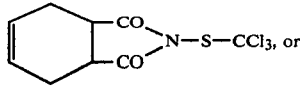

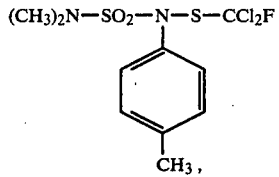

the weight ratio of component (1) to component (2) ranging from about 1:1 to 1:4.

2. A composition according to claim 1 wherein component (1) comprises

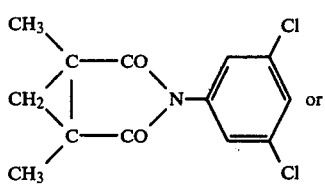

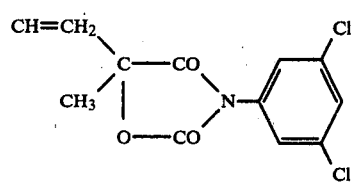

3. A composition according to claim 2 wherein component (2) comprises

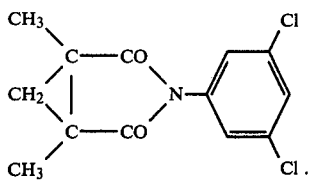

and the weight ratio of component (1) to component (2) is from about 1:1 to 1:4.

4. A composition according to claim 3, wherein component (1) comprises

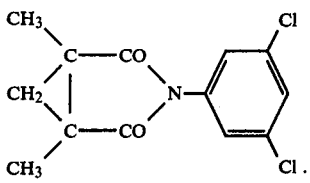

5. A composition according to claim 1, wherein component (2) comprises (CH$_3$)$_2$N—SO$_2$—N—S—CCl$_2$F 6. A composition according to claim 5, wherein component (1) comprises 7. A method of combating fungi which comprises applying to the fungi, or to a habitat thereof, a composition according to claim 1.

8. A method according to claim 7, in which the total active compounds are applied to soil in an amount of about 0.00001 to 0.1% by weight.

9. A method according to claim 7, in which the total active compounds are applied to seed in an amount of about 0.001 to 50 g per kg of seed.

* * * * *